Figure 1:
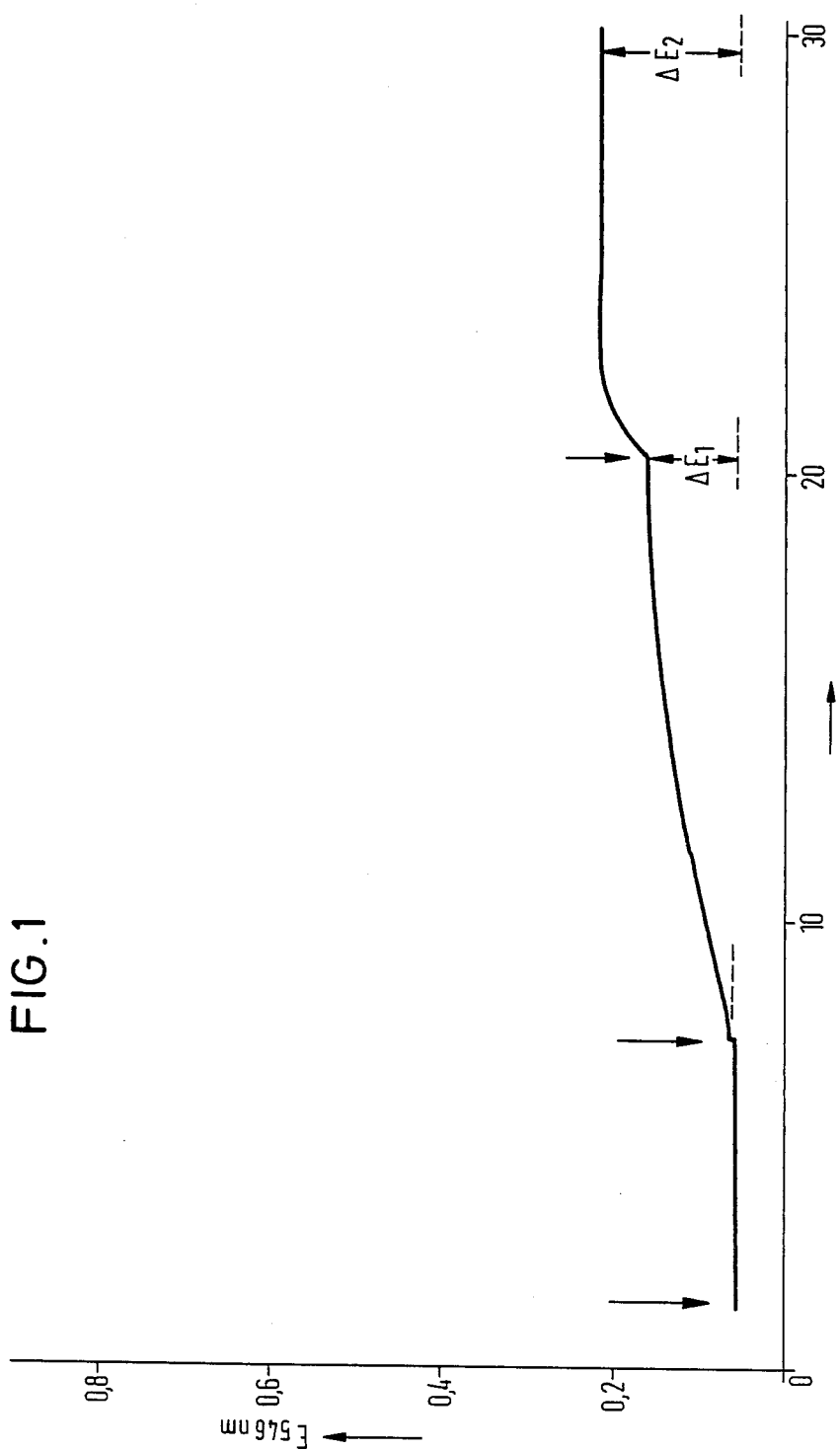

United States Patent [19]

Kerscher et al.

[11] Patent Number: 4,851,335

[45] Date of Patent: Jul. 25, 1989

[54] PROCESS AND REAGENT FOR THE SPECIFIC DETERMINATION OF HDL CHOLESTEROL IN SERUM OR PLASMA

[75] Inventors: Lorenz Kerscher, Penzberg; Joachim Siedel, Bernried; Joachim Ziegenhorn, Starnberg; Brigitte Pautz, Herrsching, all of Fed. Rep. of Germany

[73] Assignee: Boehringer Mannheim GmbH, Mannheim, Fed. Rep. of Germany

[21] Appl. No.: 908,031

[22] Filed: Sep. 16, 1986

[30] Foreign Application Priority Data

Sep. 18, 1985 [DE] Fed. Rep. of Germany ....... 3533288

[51] Int. Cl.⁴ .............................................. C12Q 1/60
[52] U.S. Cl. ......................................... 435/11; 435/28
[58] Field of Search ........................................... 435/11

[56] References Cited

U.S. PATENT DOCUMENTS

| | | | |
|---|---|---|---|
| 4,164,448 | 8/1979 | Roeschlau et al. | 435/11 |
| 4,184,921 | 1/1980 | Roeschlau et al. | 435/11 |
| 4,226,713 | 10/1980 | Goldberg | 435/11 |
| 4,366,244 | 12/1982 | Pascal | 435/11 |
| 4,414,326 | 11/1983 | Goldberg | 435/11 |
| 4,544,630 | 10/1985 | Ziegenhorn | 435/11 |

FOREIGN PATENT DOCUMENTS 0091026 10/1983 European Pat. Off. .

*Primary Examiner*—Sam Rosen
*Attorney, Agent, or Firm*—Felfe & Lynch

[57] ABSTRACT

The present invention provides a process for the specific determination of HDL cholesterol in serum or plasma by incubation with a cholesterol detection system, containing cholesterol oxidase and cholesterol esterase in a buffered aqueous medium, and measurement of a product of the cholesterol oxidase reaction or of the oxygen consumption, wherein a sample to be tested is incubated in the presence of a salt of a bile acid or of a bile acid derivative or of dioctylsulphosuccinate, a first measurement is then carried out, subsequently a non-ionic, polyethylene oxide group-containing detergent or a secondary alkane sulphonate is added, again incubated and a second measurement is carried out, the amount of HDL cholesterol being determined from the difference between the first and second measurement.

The present invention also provides a reagent for the specific determination of HDL cholesterol in serum or plasma containing cholesterol oxidase, buffer and cholesterol esterase, wherein, referred to the final solution, it contains 0.1 to 10 U/ml. cholesterol esterase
0.05 to 10 U/ml. cholesterol oxidase
20 to 500 mmole/liter buffer substance (pH 6.0 to 8.0)
0.2 to 20 mmole/liter of a salt of a bile acid or of a bile acid derivative or of dioctylsulphosuccinate and, separately therefrom,
0.02 to 2% non-ionic polyethylene oxide group-containing detergent or secondary alkane sulphonate, and optionally 0.05 to 2% of an alcohol containing up to 3 carbon atoms.

15 Claims, 2 Drawing Sheets

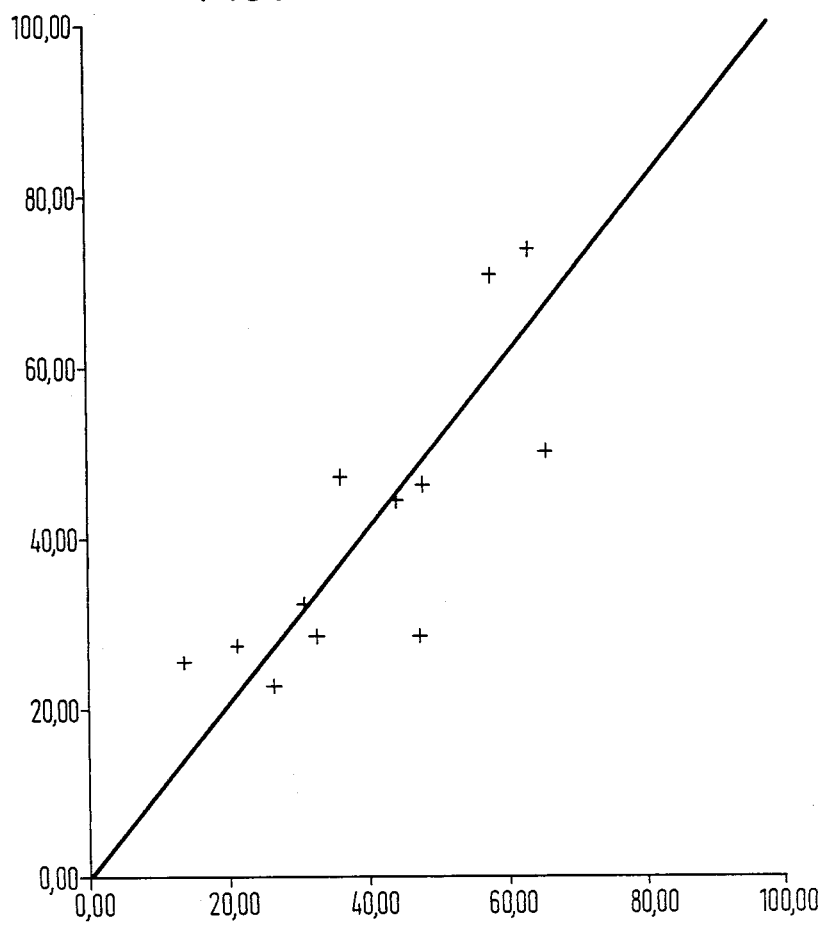

PROCESS AND REAGENT FOR THE SPECIFIC DETERMINATION OF HDL CHOLESTEROL IN SERUM OR PLASMA

The present invention is concerned with a process and reagent for the specific determination of HDL cholesterol in serum or plasma.

Besides the determination of the total cholesterol in serum (or plasma), which has long since been firmly established in the clinical laboratory, in recent years the additional analysis of the cholesterol bound to the "high density lipoprotein" fraction (HDL cholesterol) has achieved a considerable importance for the improved diagnosis of atherosclerosis or myocardial infarction risk.

Extensive clinical studies have shown that an increased level of total serum cholesterol (sum of the free and fatty acid esterified cholesterol bound to the lipoprotein fractions chylomicrons, VLDL ("very low density lipoproteins"), LDL ("low density lipoproteins"), as well as HDL) leads to an increased myocardial infarction risk, whereas, on the other hand, there is an inverse relationship between the serum HDL-cholesterol content and the danger of atherosclerotic changes of blood vessels (see e.g. G. Assmann, Lipidstoffwechsel und Atherosklerose, pub. Schattauer-Verlag, Stuttgart, 1982).

For the determination of the serum total cholesterol, for about 15 years there have been available simple but, nevertheless, very exact completely enzymatic analysis processes which can be carried out not only manually but also equally well on automated analysis systems without any sample pretreatment step and which usually proceed according to the reaction scheme:

(1)

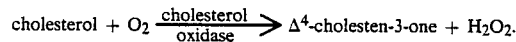

(2)

The cholesterol detection takes place either via the hydrogen peroxide formed, preferably colorimetrically and especially by the peroxidase-catalysed oxidative coupling of phenol or of phenol or aniline derivatives with 4-aminoantipyrine to give a red to violet coloured quinone-imine material ("Trinder reaction") or via the cholestenone formed or via the oxygen consumed according to equation 2). These methods of determination are known, for example, from Federal Republic of Germany Patent Specifications Nos. 22 24 132 and 25 06 712.

An important characteristic of the appropriate reaction systems or analysis reagents for the determination of total cholesterol is the presence of detergents, especially of non-ionic alkyl or alkylaryl polyethylene oxide ethers, possibly together with bile acid salts, such as sodium cholate. The detergents additionally serve as solubilising agents, without which the cholesterol esterase would not manifest any hydrolytic As cholesterol esterases, there are thereby preferably used enzymes of microbial origin.

The determination of the serum HDL cholesterol takes place according to the same principle but, for that purpose, the other cholesterol-containing lipoprotein particles (chylomicrons, VLDL and LDL) must be previously separated from the serum in one or more process steps.

For the separation of these lipoproteins, there are used, in particular, ultracentrifugation electrophoresis or diverse precipitation methods, such as immune precipitation, precipitation with phosphotungstic acid/$Mg^{2+}$, dextran sulphate/$MG^{2+}$ or heparin/$Mn^{2+}$ or with polyethylene glycol (see e.g. Arztl. Lab., 29, 107–114/1983; Clin. Chem., 31, 252–256/1985).

Besides the additional apparatus necessary herefor, these separation processes also require a considerable time and personnel expense, which makes a routine HDL-cholesterol determination in the clinical laboratory much more difficult and thus also more expensive.

Because of the equally high diagnostic value of the total cholesterol content as well as of the HDL-cholesterol content in the serum, it is, therefore, all the more important to have available a process and reagent which makes possible the analysis of HDL-cholesterol and serum total cholesterol in a reaction batch, without the necessity of a special sample preparation.

Therefore, it is an object of the present invention to provide a process for the direct carrying out of HDL-cholesterol determinations in serum or plasma without previous separation of LDL-cholesterol, VLDL-cholesterol and chylomicron cholesterol from the sample. It is a further object of the present invention to carry out such a process in combination with a total cholesterol determination in serum or plasma.

Thus, according to the present invention, there is provided a process for the specific determination of HDL-cholesterol in serum or plasma by incubation with a cholesterol detection system, containing cholesterol oxidase and cholesterol esterase in a buffered aqueous medium, and measurement of a product of the cholesterol oxidase reaction or of the oxygen consumption, wherein a sample to be tested is incubated in the presence of a salt of a bile acid or of a bile acid derivative or of dioctylsulphosuccinate (Aerosol ® OT), a first measurement is then carried out, subsequently a non-ionic, polyethylene oxide group-containing detergent or a secondary alkane sulphonate is added, again incubated and a second measurement is carried out, the amount of HDL cholesterol being determined from the difference between the first and second measurement.

The present invention is based upon the surprising ascertainment that certain detergents only make available to the reaction with cholesterol esterase and cholesterol oxidase the cholesterol contained in the chylomicrons, VLDL and LDL so that it is possible to allow these cholesterol fractions to react of in a first incubation step with the said enzymes and only then, in a second incubation step, by the addition of a non-ionic, polyethylene oxide group-containing detergent, or of a secondary alkane sulphonate, to introduce the HDL cholesterol to the reaction. This makes possible, in a single reaction batch, either first to determine the cholesterol contained in the chylomicrons, VLDL and LDL and thereafter separately the HDL cholesterol, so that there is obtained not only total cholesterol but also HDL cholesterol in a single batch, or the chylomicron, VLDL and LDL cholesterol is first allowed to react off without determination and then only the amount of HDL cholesterol is measured. In the first case, the amount of HDL cholesterol is determined from the difference between the measurements after the first incubation and the second incubation and the total amount of cholesterol from the measurement after the second incubation alone. In the second case, for the sole determination of HDL cholesterol, during the first incubation, a phenol or a phenol or aniline derivative, as well as peroxidase, are present but no aminoantipyrine, 3-methyl-2-benzothiazolinone hydrazone (MBTH) or its sulphonated derivative (MBTH-S). The hydrogen peroxide formed according to equation,2) thereby reacts off without colour formation. Colour is only formed when carrying out the second incubation in the presence of 4-aminoantipyrine (4-AAP), MBTH or MBTH-S which is a direct measure for the HDL concentration. Consequently, in the case of this process modification, only one measurement is necessary for the HDL determination.

Therefore, the process according to the present invention is preferably carried out in such a manner that a cholesterol detection system is used which measures hydrogen peroxide as a product of the cholesterol oxidase reaction (2) by colour formation. Appropriate chromogenic systems which can be used for the hydrogen peroxide detection are well known. The so-called Trinder system is preferred which consists of phenol or a phenol derivative or a substituted aniline, 4-aminoantipyrine and peroxidase. Amongst the phenol compounds which can be used, phenol itself, as well as chlorophenol, triiodo- and tribromohydroxybenzoic acid and dichlorophenolsulphonic acid have achieved especial importance. Instead of 4-aminoantipyrine, there can also be used, for example, 3-methyl-2-benzothiazolinone hydrazone (MBTH) and its sulphonated derivative (MBTHS), preferably in combination with a substituted aniline, such as dimethylaniline, dimethylaminobenzoic acid, N-ethyl-N-$\beta$-sulphoethyl-m-toluidine or N-ethyl-N-$\beta$-hydroxyethyl-m-toluidine, the last two compounds also having proved to be useful in combination with 4-aminoantipyrine.

As cholesterol esterase, there can be used a microbial cholesterol esterase, for example from *Candida cylindracea*, or the pancreatic enzyme, which is preferred.

As bile acids or bile acid derivatives are to be mentioned the alkali metal and magnesium salts of cholic acid, desoxycholic acid, lithocholic acid, taurocholic acid, glycocholic acid, desoxyglycocholic acid and desoxytaurocholic acid and choleic acids, sodium cholate being preferred. Alternatively, there can also be used sodium dioctylsulphosuccinate (Aerosol ® OT). We have found that these detergents only digest the lipid-rich lipoproteins provided with a relatively small protein part, i.e. chylomicrons, VLDL and LDL, and make available for the enzymatic reaction the cholesterol contained in them.

The cholesterol of the HDL fraction is made available to the enzymatic determination by non-ionic, polyethylene oxide group-containing detergents, such as the non-ionic alkyl or alkylaryl polyethylene oxide ethers, for example n-dodecyl polyethylene glycol ether (Thesit ®), isotridecanol polyethylene oxide ether (Genapol ® x-80) and isooctylphenyl polyethylene oxide (Triton ® X-100). Anionic secondary alkane sulphonates, such as are, for example, commercially available under the name Hostapur ®, can also be used. These HDL-digesting detergents are preferably employed together with methanol, ethanol, n-propanol or isopropanol, propanol preferably being used. The amount of alcohol used is preferably from 0.05 to 2%. These and all other statements of concentration given herein refer to the end concentration in the reaction mixture.

The salt of the bile acid or of the bile acid derivative is preferably added in a concentration of from 0.2 to 20 mmole/liter. However, these amounts can be gone below or exceeded, depending upon the sample to be investigated. The same applies to the dioctylsulphosuccinate.

With regard to the second detergent, i.e. the non-ionic polyethylene oxide group-containing detergent or the secondary alkane sulphonate, the preferred concentration is from 0.02 to 2%. However, depending upon the sample, these concentrations can also be gone below or exceeded.

For the rest, when carrying out the process according to the present invention, as in the case of previously known cholesterol determinations, the pH value and buffer substances used are those appropriate for the amounts of enzyme used.

The present invention also provides a reagent for the specific determination of HDL cholesterol in serum, containing cholesterol esterase, cholesterol oxidase and buffer, wherein, referred to the final aqueous solution, it contains 0.1 to 10 U/ml. cholesterol esterase,
0.05 to 10 U/ml. cholesterol oxidase
20 to 500 mmole/liter of buffer substance (pH 6.0 to 8.0),
0.2 to 20 mmole/liter of a salt of a bile acid or bile acid derivative or dioctylsulphosuccinate and, separately therefrom,
0.02 to 2% non-ionic polyethylene oxide group-containing detergent or secondary alkane sulphonate, as well as optionally
0.05 to 2% of an alcohol containing up to 3 carbon atoms.

According to a first embodiment, the reagent according to the present invention contains 0.05 to 20 U/ml. peroxidase, 0.2 to 20 mmole/liter of a phenol or aniline and optionally 0.02 to 5% polyethylene glycol and/or 0.05 to 2% n-propanol.

A preferred reagent according to the present invention contains 0.2 to 2 U/ml. cholesterol esterase, 0.05 to 0.5 U/ml. cholesterol oxidase, 1 to 5 U/ml. peroxidase, 50 to 200 mmole/liter potassium phosphate buffer (pH 6.5 to 7.0), 1.4 to 10 mmole/liter phenol or phenol derivative, 1 to 5 mmole/liter of a salt of a bile acid or bile acid derivative or dioctylsulphosuccinate, optionally separately therefrom 0.2 to 2 mmole/liter 4-aminoantipyrine and separately from the other components, except possibly from the 4-aminoantipyrine, 0.5 to 5.0% non-ionic, polyethylene group-containing detergent or secondary alkane sulphonate and optionally 0.1 to 0.5% n-propanol and 0.5 to 5.0% polyethylene glycol.

In a further embodiment, the reaction components can be impregnated on or in a carrier material. The carrier material used can be an absorbent or swellable or film-forming carrier material, such as paper or a similar fleece material, for example tea bag paper. The reaction components can thereby be distributed on several carriers which are in contact with one another.

By means of the present invention, the cholesterol contained in the HDL can be determined directly without previous separation from other cholesterol-containing lipoprotein fractions. This means a substantial easing and simplification of the determination methods.

The following Examples are given for the purpose of explaining the present invention, the following abbreviations thereby being used:

CHOD=cholesterol oxidase

CHOL=esterase cholesterol esterase
POD=peroxidase
4=AAP 4-aminoantipyrine
PEG 6000 polyethylene glycol 6000
TRA triethanolamine

EXAMPLE 1

(a) Basic reagent: potassium phosphate 0.1 mole/liter (pH 6.7)
3 mM sodium cholate
0.8 mM 4-AAP
1.2 U/ml. CHOD
0.5 U/ml. CHOL esterase
1.4 mM phenol
0.1% PEG 6000
3 U/ml. POD
(b) Start reagent for the TRA buffer 0.05M, pH 7.1
second step : 10% Thesit
10% propanol
(c) Performance of the test:
wavelength: 546 nm
temperature: 25° C.
measurement at 25° C. against reagent blank
Into cuvettes with an optical pathlength of 10 mm., pipette:

|  | sample | reagent blank (RB) |
| --- | --- | --- |
| basic reagent | 2.00 ml. | 2.00 ml. |
| sample | 0.02 ml. | — |
| water | — | 0.02 ml. |
| incubate 10 (−30) minutes, subsequently measure $E_1$ (sample) against $E_1$ (RB) | | |
| start reagent | 0.02 ml. | 0.02 ml. |
| incubate at least a further 10 minutes, subsequently measure $E_2$ (sample) against $E_2$ (RB) (= $E_2$) | | |

(d) Calculation
The calculation takes place by simultaneously using a serum standard with a known total and HDL cholesterol concentration, the serum standard thereby being used in the test batch in the same way as the sample $$c\ [\text{total cholesterol}](mg/dl) = c_{standard} \times \frac{\Delta E_2 \text{ sample}}{\Delta E_2 \text{ standard}}$$

$$c\ [\text{HDL cholesterol}](mg/dl) = c_{standard} \times \frac{(\Delta E_2 - \Delta E_1)\ \text{sample}}{(\Delta E_2 - \Delta E_1)\ \text{standard}}$$

The time course of the stepwise colour formation taking place corresponding to the test batch according to the Example is reproduced in FIG. 1 of the accompanying drawings.

EXAMPLE 2

(a) Basic reagent: as in Example 1 but without 4-AAP
(b) Start reagent: as in Example 1 but additionally with 80 mM 4-AAP
(c) Performance of the test:
wavelength: 546 nm
temperature: 25° C.
measurement at 25° C. against reagent blank
Into cuvettes with an optical pathlength of 10 mm., pipette:

|  | sample | reagent blank (RB) |
| --- | --- | --- |
| basic reagent | 2.00 ml. | 2.00 ml. |
| sample | 0.02 ml. | — |
| water | — | 0.02 ml. |
| incubate 10 (−30) minutes | | |
| start reagent | 0.02 ml. | 0.02 ml. |
| incubate at least for further 10 minutes, subsequently measure E (sample) against E (RB) (= ΔE) | | |

(d) Calculation:
The calculation takes place by simultaneously using a serum standard with a known total and HDL cholesterol concentration, the serum standard thereby being used in the test batch in the same way as the sample $$c\ [\text{HDL cholesterol}](mg/dl) = c_{standard} \times \frac{\Delta E\ \text{sample}}{\Delta E_{standard}}$$

A comparison of the HDL cholesterol determination according to Example 2 in various human sera using the process according to the present invention with the method using a phosphotungstic acid (PTA)/Mg sulphate precipitation is illustrated in FIG. 2 of the accompanying drawings. The method comparison gives a regression of Y=−0.907+1.019 X with a correlation coefficient of 0.814.

Identical results for HDL cholesterol are obtained when working according to Example 1.

We claim:
1. In a process for the specific determination of HDL cholesterol in serum or plasma sample by incubation in a reaction medium including a cholesterol detection system, containing cholesterol oxidase and cholesterol esterase in a buffered aqueous medium, followed by measurement of a product of the cholesterol oxidase reaction or of the oxygen consumption, the improvement comprising
first incubating the sample to be tested with the cholesterol detecting system in the presence of a salt of a bile acid or of a bile acid derivative or of dioctylsulphosuccinate, and measuring a first amount of cholesterol, subsequently adding a non-ionic, polyethylene oxide group-containing detergent or a secondary alkane sulphonate and again incubating and measuring to determine a second amount of cholesterol, the amount of HDL cholesterol being determined from the difference between the first and second amounts of cholesterol measured.

2. The process of claim 1, wherein the cholesterol detection system reacts with the hydrogen peroxide product of the cholesterol oxidase reaction to form a colour which is measured.

3. The process of claim 2, wherein, for the colour formation, there is used a chromogenic system containing a phenol or an aniline, 4-1-aminoantipyrine and peroxidase.

4. The process of claim 1, wherein the first incubating step is carried out in the presence of
phenol or aniline and
peroxidase, and the second incubation is carried out in the presence of 4-aminoantipyrine.

5. The process of claim 1 wherein cholesterol esterase from the pancreas is used.

6. The process of claim 1 wherein 0.2 to 20 mmole/liter of the salt of a bile acid or of the bile acid derivative or dioctylsulphosuccinate is used.

7. The process of claim 1 wherein 0.2 to 2% of the non-ionic polyethylene oxide group-containing detergent or the secondary alkane sulphonate is used.

8. The process of claim 1 wherein the reaction medium is at a pH of from 6.0 to 8.0.

9. The process of claim 1 wherein an alcohol containing up to 3 carbon atoms is added to the reaction medium in an amount of from 0.05 to 2%.

10. Reagent kit for the specific determination of HDL cholesterol in serum or plasma, comprising a first reagent containing cholesterol esterase, cholesterol oxidase, a buffer substance of pH 6.0 to 8.0, and a member of the group consisting of a bile acid, a bile acid derivative and dioctylsulphosuccinate; and a second reagent separated from said first reagent which contains one of a non-ionic polyethylene oxide group containing detergent or a secondary alkane sulphonate.

11. Reagent kit of claim 10, wherein said first reagent further comprises a peroxidase, and one of a phenol, a phenol derivative, or aniline.

12. Reagent kit of claim 10, wherein said second reagent further comprises a 1–3 carbon atom containing alcohol.

13. Reagent kit of claim 12, wherein said alcohol is propylene glycol or n-propanol.

14. Reagent kit of claim 10, wherein one of said first and second reagents further comprises aminoantipyrine.

15. Reagent kit of claim 10, further comprising a third reagent containing aminoantipyrine.

* * * * *

UNITED STATES PATENT AND TRADEMARK OFFICE
CERTIFICATE OF CORRECTION

PATENT NO. : 4,851,335
DATED : July 25, 1989
INVENTOR(S) : Lorenz Kerscher, et al.

It is certified that error appears in the above-identified patent and that said Letters Patent is hereby corrected as shown below:

Column 1, line 62: after "hydrolytic" insert -- activity --.

Column 2, line 52: change "of" to -- off --.

Column 5, line 1: delete first "esterase".

Column 5, line 3: change "=AAP" to -- AAP= --.

Column 5, line 4: after first "6000" add -- = --.

Column 5, line 5: after "TRA" add -- = --.

Claim 3, line 3: change "4-1-aminoantipyrine" to -- 4-aminoantipyrine --.

Signed and Sealed this

Seventeenth Day of July, 1990

Attest:

HARRY F. MANBECK, JR.

*Attesting Officer*

*Commissioner of Patents and Trademarks*